United States Patent
Nakanishi et al.

(10) Patent No.: US 6,797,245 B2
(45) Date of Patent: Sep. 28, 2004

(54) APPARATUS FOR WASHING AND DISINFECTING-STERILIZING ENDOSCOPE

(75) Inventors: Nobuyuki Nakanishi, Sagamihara (JP); Daisaku Negoro, Saitama-ken (JP); Naoya Taya, Hino (JP); Hitoshi Hasegawa, Yokohama (JP); Eiri Suzuki, Sagamihara (JP); Hisashi Kuroshima, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 10/145,008

(22) Filed: May 13, 2002

(65) Prior Publication Data

US 2002/0182105 A1 Dec. 5, 2002

Related U.S. Application Data

(62) Division of application No. 09/253,860, filed on Feb. 22, 1999, now abandoned.

(30) Foreign Application Priority Data

Mar. 26, 1998 (JP) .......................................... 10-079337
Mar. 31, 1998 (JP) .......................................... 10-085895
Oct. 27, 1998 (JP) .......................................... 10-305476

(51) Int. Cl.⁷ ............................................... A61L 9/00
(52) U.S. Cl. ............................. 422/300; 134/2; 134/26; 134/22.11; 134/22.14; 422/105; 422/116; 422/292; 422/297; 422/301
(58) Field of Search ................................. 422/105, 300, 422/116, 292, 297, 301; 134/26, 2, 22.11, 22.14

(56) References Cited

U.S. PATENT DOCUMENTS

| | | | |
|---|---|---|---|
| 4,589,403 A | 5/1986 | Ouchi et al. | |
| 4,862,872 A | 9/1989 | Yabe et al. | |
| 5,116,575 A | 5/1992 | Badertscher et al. | |
| 5,234,832 A | 8/1993 | Disch et al. | |
| 5,408,991 A | 4/1995 | Iida et al. | |
| 5,425,815 A | 6/1995 | Parker et al. | |
| 5,443,801 A | 8/1995 | Langford | |
| 5,489,531 A | 2/1996 | Benson | |
| 5,558,841 A | 9/1996 | Nakagawa et al. | |
| 5,882,589 A * | 3/1999 | Mariotti ....................... | 422/28 |
| 6,015,529 A | 1/2000 | Lin et al. | |

FOREIGN PATENT DOCUMENTS

| | | |
|---|---|---|
| DE | 3639322 C2 | 5/1988 |
| DE | 3816734 A1 | 11/1989 |
| JP | 63-260523 | 10/1988 |
| JP | 63-309236 | 12/1988 |
| JP | 10-258019 A | 9/1998 |
| WO | WO 93/24046 | 12/1993 |
| WO | WO 98/29028 A1 | 7/1998 |

* cited by examiner

*Primary Examiner*—Krisanne Jastrzab
(74) *Attorney, Agent, or Firm*—Frishauf, Holtz, Goodman & Chick, P.C.

(57) ABSTRACT

A washing vessel capable of housing an endoscope is formed in an apparatus body. A washing solution containing a detergent is spurted against the endoscope arranged within the washing vessel for washing the endoscope. Also, an oxide-based disinfecting-sterilizing solution is supplied into the washing vessel for disinfecting-sterilizing the endoscope after the washing step together with the washing vessel.

13 Claims, 10 Drawing Sheets

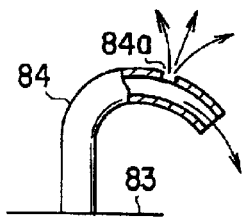
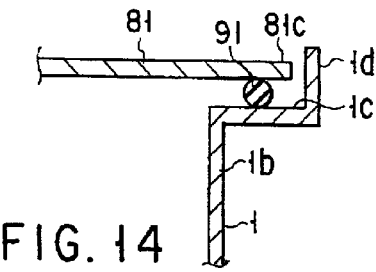
FIG. 13    FIG. 14
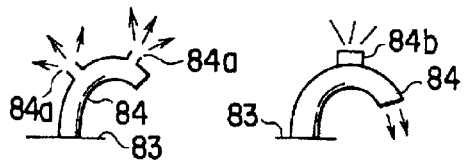 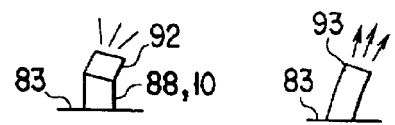
FIG. 15A    FIG. 15B    FIG. 15C    FIG. 15D
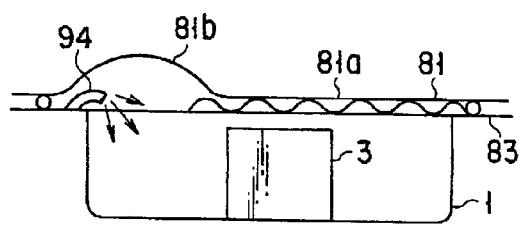
FIG. 16
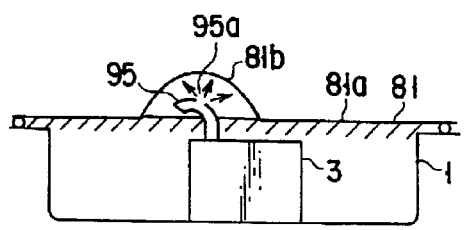
FIG. 17

APPARATUS FOR WASHING AND DISINFECTING-STERILIZING ENDOSCOPE

CROSS-REFERENCE TO RELATED APPLICATIONS

This is a divisional of application Ser. No. 09/253,860 filed on Feb. 22, 1999 now abandoned, the entire disclosure of which is incorporated hereby reference.

BACKGROUND OF THE INVENTION

The present invention relates to an apparatus for washing and disinfecting-sterilizing an endoscope.

An endoscope for medical treatment must be washed, disinfected and sterilized every time the endoscope is used. In the conventional washing-disinfecting apparatus, the endoscope is set in a washing vessel and then, a washing solution is spurted from a spurting nozzle mounted within the washing vessel against the endoscope. At the same time, the washing solution is supplied into the tubular passageway of the endoscope so as to wash the endoscope. Then, the endoscope is dipped in a disinfecting-sterilizing solution, and the solution is supplied into the tubular passageway of the endoscope so as to disinfect and sterilize the endoscope.

Further, clean water is spurted against the endoscope and supplied into the tubular passageway of the endoscope so as to perform the rinsing. Finally, air is supplied into the tubular passageway of the endoscope so as to dry the inner space of the tubular passageway. It is also known in the art that, in place of using a spurting nozzle, the endoscope is dipped in a washing solution stored in a washing vessel so as to wash the endoscope.

In another type of the apparatus, warm water is spurted from a spurting nozzle for washing the endoscope, followed by spurting from a spurting nozzle a disinfecting-sterilizing solution against the endoscope so as to disinfect and sterilize the endoscope.

In the former apparatus for washing and sterilizing the endoscope, glutaric aldehyde is used as a disinfecting-sterilizing agent. This sterilizing agent produces the prominent function of sterilizing various bacteria and viruses, but requires a long treatment time. For example, the sterilizing agent is said to require 45 minutes of the disinfecting time and 10 hours of the sterilizing time. Therefore, in inspections in which sufficient treating time cannot be allowed, it is unavoidable to shorten the treating time, leading to an insufficient disinfecting-sterilizing effect. Alternatively, the number of inspections must be decreased.

Also, the disinfecting-sterilizing agent of glutaric aldehyde must be diluted in advance to have a predetermined concentration, and the diluted disinfecting-sterilizing agent must be injected in an amount of about 20 L (liters) into the washing-disinfecting apparatus. In performing the injecting operation, an activating agent is added to about 3 to 5L of the disinfecting-sterilizing solution, followed by shaking the resultant solution 4 to 6 times and subsequently injecting the solution into the washing-disinfecting apparatus. These operations give a big burden to the user.

In the latter apparatus for washing and sterilizing an endoscope, the washing solution and the disinfecting-sterilizing solution are used in a warmed condition. Naturally, the warming takes a long time, leading to a long washing-disinfecting time. Also, requirement of the warming means leads to a high washing-disinfecting cost. Further, in order to allow the spurted disinfecting-sterilizing agent to permeate into the endoscope without fail, the endoscope must be set over a large space so as to prevent parts of the endoscope from overlapping each other. As a result, the washing-disinfecting apparatus is rendered bulky.

It should also be noted that the disinfecting sterilizing agent, which is spurted, is unlikely to permeate into fine portions of the endoscope, making it necessary to perform the disinfecting-sterilizing step for a long time. A disinfecting-sterilizing agent of glutaric aldehyde type is also used in the washing disinfecting apparatus of this type. Since the disinfecting-sterilizing agent must be warmed, the agent is promptly deteriorated, making it necessary to discard the remaining agent every day. As a result, the operating cost is increased.

The endoscope includes various kinds including, for example, an endoscope for stomach, an endoscope for duodenum, an endoscope for large-intestine, and an endoscope for bronchia. The endoscope for stomach does not include a special tubular passageway. Also, the tubular passageway is short and a has an appropriate thickness. Therefore, the washing and water removal can be performed in a short time. On the other hand, the endoscope for duodenum has a very thin tubular passageway and requires a long washing time, making it necessary to use a pipe for rising the forceps. Also, it is necessary to introduce high pressure air into the tubular passageway for removing water.

The endoscope for large intestine includes a long inserting section and a thick tubular passageway, making it necessary to wash the endoscope and remove water from the endoscope carefully and sufficiently. Further, the endoscope for bronchia has a fine tubular passageway. The endoscope can be washed easily in a short time. Also, water removal from the endoscope can be performed easily. However, the tubercle bacillus attached to the bronchia has a high resistance to chemicals, making it necessary to carry out the disinfection-sterilization for a long time.

AS described above, the endoscopes differ from each other in construction depending on kind. If these endoscopes are washed and sterilized under the same conditions, the washing-disinfecting is insufficient in some kinds of endoscopes and is excessive in other kinds of endoscopes so as to give detrimental effects to the endoscopes. Also, it is undesirable in economy to perform an excessive washing-disinfecting operation.

The conventional apparatus for washing-disinfecting an endoscope includes a washing vessel and holding sections mounted within the washing vessel for holding a plurality of endoscopes. A detection switch is mounted to each of the holding sections. If endoscopes to be washed are set on the holding sections within the washing vessel, the detection switches are turned on so as to detect the kind of endoscope based on the number of endoscopes set on the holding sections, the thickness of the inserting section of the endoscope, etc. Also, the treatment times for the washing, disinfecting-sterilizing, rinsing and water-removing steps are set in accordance with the number and kinds of endoscopes.

In the conventional apparatus, however, the washing-disinfecting conditions are set on the basis of the number of endoscopes set in the washing vessel. Also, the washing-disinfecting conditions are set by detecting the kind of endoscope depending on the thickness of the endoscope. In the conventional apparatus, it is certainly possible to detect the kinds of endoscopes such as those for stomach, for duodenum, for large intestine or for bronchia. However, new endoscopes differing from the conventional endoscopes in thickness, shape and construction are being developed successively, making it difficult to accurately detect the kind of endoscope.

It should also be noted that the washing vessel, particularly the ceiling of the washing vessel, is contaminated during the washing step of the endoscope, making it necessary to wash the ceiling of the washing vessel while washing the endoscope. Therefore, a nozzle for washing the ceiling is also mounted within the washing vessel to allow the washing solution to be spurted from the nozzle against the ceiling of the washing vessel. Incidentally, the washing solution used for washing the endoscope and the ceiling is circulated by using a pump so as to use the washing solution again to reduce the operation costs and for environmental concerns.

Since the washing solution used for washing the endoscope is reused to wash the ceiling of the washing vessel, it is possible for the washing solution of the ceiling to contain a large amount of contaminants such as bacteria. Naturally, these contaminants tend to be blown against the ceiling together with the washing solution. Also, if the pressure for spurting the washing solution against the ceiling is not sufficiently high, it is impossible to sufficiently wash away the contaminants such as bacteria attached to the ceiling of the washing vessel. It is also difficult to sufficiently remove the washing solution attached to the ceiling in the rising step for removing the washing solution.

Needless to say, the ceiling of the washing vessel must be kept clean. Otherwise, the contaminants such as bacteria attached to the ceiling tend to be transferred onto the endoscope set in the washing vessel. It follows that the endoscope once washed and disinfected tends to be contaminated again.

Under the circumstances, the washing vessel is not washed in the washing step by the washing means mounted within the washing vessel, and the washing of the washing vessel by the washing means mounted within the washing vessel is performed after the washing step so as to remove without fail the contaminants attached to the ceiling of the washing vessel and, thus, to prevent the endoscope from being contaminated with the contaminants coming from the ceiling.

However, the wall or ceiling of the washing vessel has a large area, making it difficult to uniformly spray the wall or ceiling with the washing solution. Also, it is necessary to use additional equipment for the spraying, leading to a high apparatus cost and to the complex structure of the apparatus.

BRIEF SUMMARY OF THE INVENTION

An object of the present invention is to provide an apparatus and method for washing and disinfecting-sterilizing an endoscope in a short time without fail.

According to an aspect of the present invention, there is provided an apparatus for washing and disinfecting-sterilizing an endoscope, comprising a vessel in which an endoscope can be mounted, washing solution supply means for supplying a washing solution for washing an endoscope into the vessel, washing means for washing the endoscope mounted within the vessel with the washing solution, and disinfecting-sterilizing solution supply means for supplying an oxide-based disinfecting-sterilizing solution into the vessel, wherein the endoscope mounted within the vessel is disinfected and sterilized with the oxide-based disinfecting-sterilizing solution.

According to another aspect of the present invention, there is provided a method of washing-disinfecting-sterilizing an endoscope, comprising the steps of supplying a washing solution into a vessel having an endoscope mounted therein for washing the endoscope, and supplying an oxide-based disinfecting-sterilizing solution into the vessel so as to disinfect-sterilize the endoscope with the disinfecting-sterilizing solution.

In the method of the present invention, the entire endoscope is washed with a washing solution containing as a main component an alkaline or enzyme-based detergent, followed by disinfecting-sterilizing the entire endoscope with an oxide-based disinfecting-sterilizing solution. The oxide-based disinfecting-sterilizing solution exhibits a high sterilizing power, making it possible to shorten markedly the time for the disinfecting-sterilizing step, compared with use of the conventional disinfecting-sterilizing solution.

According to still another aspect of the present invention, there is provided An apparatus for washing and disinfecting-sterilizing an endoscope by dipping an endoscope in a washing solution or disinfecting-sterilizing solution stored in a vessel, comprising, reading means for reading data stored in the endoscope, and setting means for setting the conditions for washing and disinfecting the endoscope based on the data read by the reading means.

Various data such as the kind of the endoscope, the date of manufacture and the date of delivery, which are stored in the endoscope, are read out by the reading apparatus so as to set the conditions for washing and disinfecting-sterilizing the endoscope, making it possible to perform the washing and disinfecting-sterilizing appropriately for each of the endoscopes.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 13 is a side view showing a disinfecting nozzle included in the apparatus according to the sixth embodiment of the present invention;

FIG. 14 is a cross sectional view showing in a magnified fashion a portion XIV shown in FIG. 12;

FIGS. 15A to 15D show modifications of the apparatus according to the sixth embodiment of the present invention;

FIG. 16 shows the construction of an apparatus for washing and disinfecting-sterilizing an endoscope according to a seventh embodiment of the present invention;

FIG. 17 shows the construction of an apparatus for washing and disinfecting-sterilizing an endoscope according to a eighth embodiment of the present invention;

DETAILED DESCRIPTION OF THE INVENTION

Let us describe an apparatus for washing and disinfecting-sterilizing an endoscope according to the first embodiment of the present invention with reference to FIGS. 1 to 4.

Figure 1:
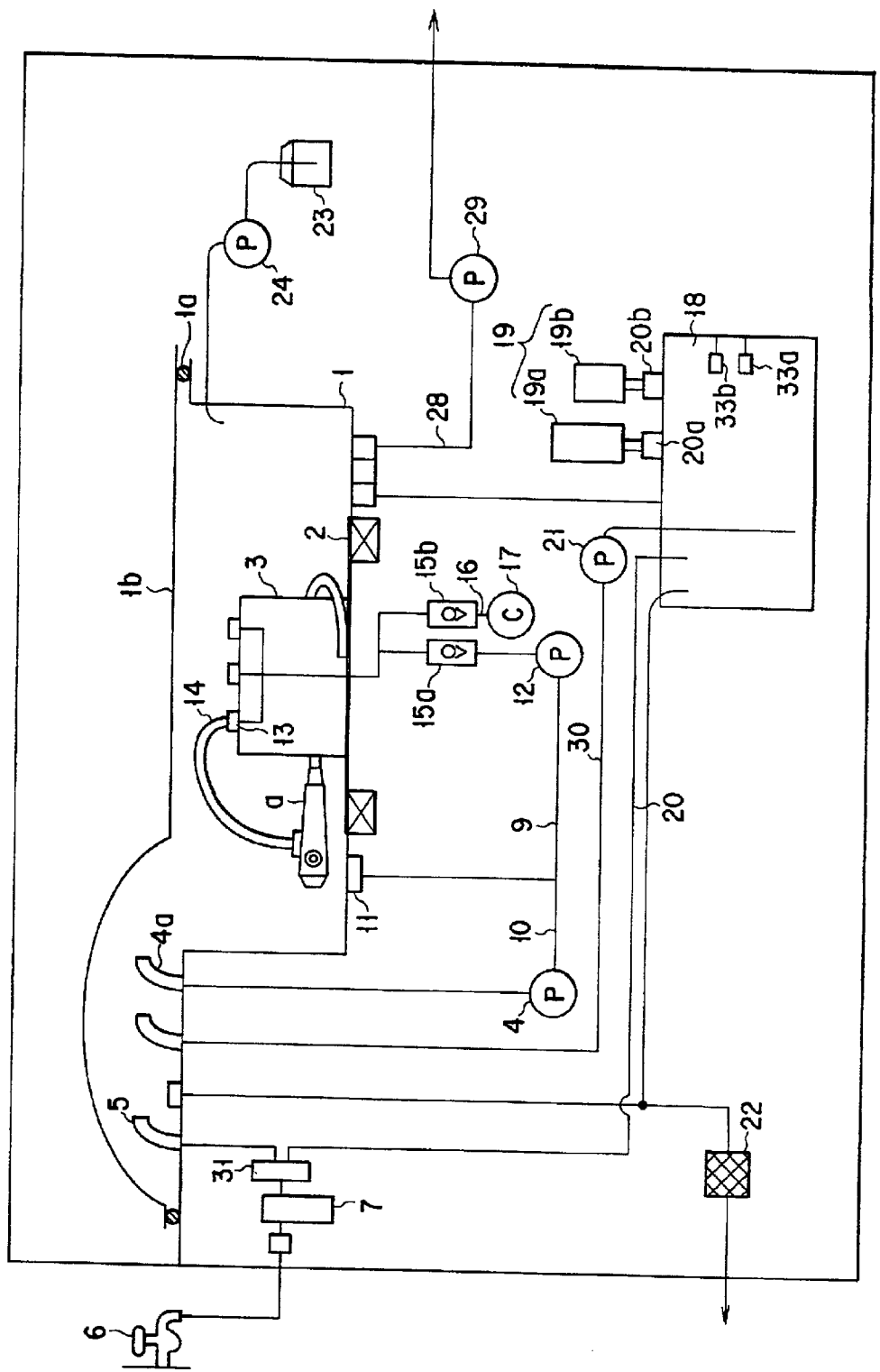
FIG. 1 shows the entire construction of an apparatus for washing and disinfecting-sterilizing an endoscope according to a first embodiment of the present invention.

Specifically, FIG. 1 shows the entire construction of the apparatus. As shown in the drawing, an endoscope a is arranged inside a washing vessel 1. A vibrating plate 2 provided with a Ranjuban type ultrasonic oscillator is arranged within the washing vessel 1. An ultrasonic vibration is oscillated from the vibrating plate 2 into the washing liquid housed in the washing vessel 1 so as to wash the outer surface of the endoscope a including fine clearances formed in the outer surface.

A tower 3 is arranged in a central portion of the washing vessel 1 for decreasing the amount of the washing solution housed in the washing vessel 1. The upper open portion of the washing vessel 1 is closed by a lid 1b having a packing 1a extending along the outer circumferential surface so as to keep the washing vessel liquid-tight and gas-tight. Also arranged within the washing vessel 1 is a washing solution nozzle 4a communicating with the discharge port of a washing solution pump 4 via a washing solution tubular passageway 10. A high pressure washing solution is spurted from the nozzle 4a so as to wash the outer surface of the endoscope a. Further, a washing water nozzle 5 for supplying city water into the washing vessel 1 is arranged near the washing solution nozzle 4a. The nozzle 5 is connected to a plug 6 of city water with a bacteria-removing filter 7 interposed therebetween.

A tubular passageway 9 for washing the inner passageway of the endoscope and the washing solution tubular passageway 10 are mounted to the washing-disinfecting apparatus body. The suction sides of these tubular passageways 9 and 10 communicate with a circulating liquid suction port 11 at the bottom portion of the washing vessel 1.

The other end of the tubular passageway 9 for washing the inner passageway of the endoscope is connected to a pump 12 for washing the inner passageway of the endoscope. The pump 12 is connected to a channel connection port 13 with a check valve 15a interposed therebetween. The channel connection port 13 is connected to various channels within the endoscope a via a tube 14 for washing the inner passageway of the endoscope. Further, an air supply tubular passageway 16 is connected to the tubular passageway 9 for washing the inner passageway of the endoscope, said tubular passageway 9 being connected to the channel connection port 13. As shown in the drawing, a check valve 15b is mounted to the air supply tubular passageway 16. Still further, a compressor 17 is connected to the air supply tubular passageway 16. It follows that the compressed air is supplied from the compressor 17 into the various channel connection port 13 of the endoscope a so as to remove water from within the endoscope a.

Bottles 19 housing concentrated disinfecting-sterilizing agents are set above a disinfecting solution tank 18. A single or a plurality of bottles 19 are set above the tank 18 depending on the kinds of the concentrated disinfecting-sterilizing agents.

The disinfecting-sterilizing solution is an oxide-based disinfecting solution containing as a main component acetic peracid or hydrogen peroxide. For preparing the disinfecting-sterilizing solution, a single or a plurality of chemicals are mixed and, then, diluted with clean water to activate the solution so as to allow the diluted solution to produce a sterilizing effect.

Figure 2A:
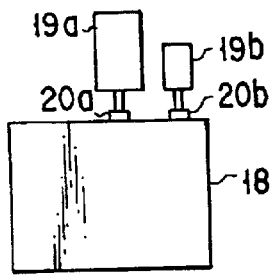
FIGS. 2A to 2C show the arrangement of solution bottles used in the apparatus according to the first embodiment of the present invention.
Figure 2B:
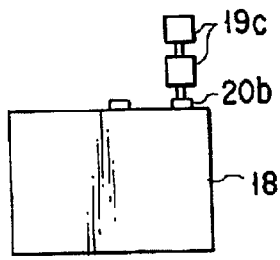
Figure 2C:
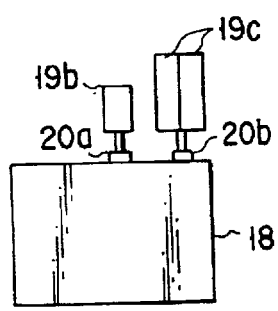
Figure 4:
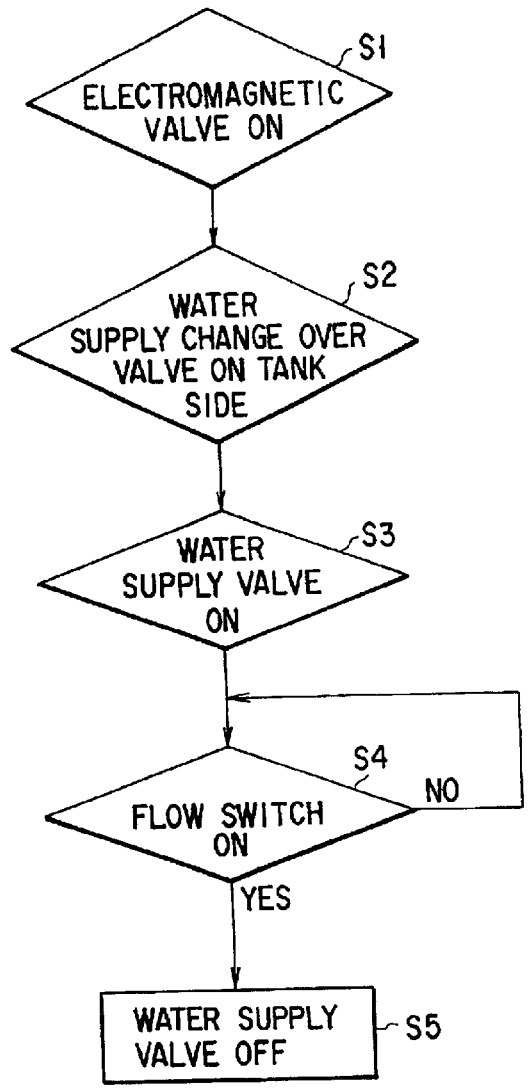
FIG. 4 is a flow chart showing the operation of the apparatus according to the first embodiment of the present invention.

Various types of disinfecting-sterilizing solutions are used in the present invention including, for example, a combination of a main agent 19a and an activating agent 19b as shown in FIG. 2A, a combination of two kinds of main agents 19c as shown in FIG. 2B, and a combination of two kinds of main agents 19c and the activating agent 19b as shown in FIG. 2C.

Electromagnetic valves 20a, 20b mounted to the bottles 19 are opened to permit the concentrated chemicals housed in the bottles 19 to fall gravitationally ally into the disinfecting-sterilizing solution tank 18, followed by operating a button of a main panel so as to prepare a desired disinfecting-sterilizing solution.

Figure 3:
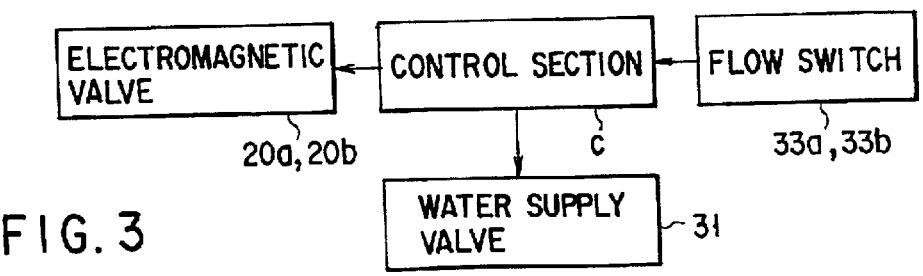
FIG. 3 is a block diagram showing the operation of the apparatus according to the first embodiment of the present invention.

Float switches 33a, 33b are mounted in the disinfecting-sterilizing tank 18, and a water-supply valve 31 consisting of an electromagnetic valve is mounted to a tubular passageway for supplying water into the disinfecting-sterilizing tank 18. As shown in FIG. 3, the float switches 33a, 33b are connected to a control section C to allow the electromagnetic valves 20a, 20b and the water supply valve 31 to be turned on or off by a signal generated from the float switches 33a, 33b.

To be more specific, when the electromagnetic valves 20a, 20b are turned on (step S1), the concentrated disinfecting-sterilizing solution falls into the disinfecting-sterilizing tank 18, followed by changing-over the water supply valve 31 on the tank side (step S2). Then, the water supply valve 31 is turned on, with the result that city water is supplied through the water supply filter 7 into the disinfecting-sterilizing tank 18 (step S3).

Then, the float switch 33a within the disinfecting-sterilizing tank 18 is turned on (step S4). When a predetermined water level is reached, the water supply valve 31 is closed (step S5). In this fashion, the disinfecting-sterilizing solution of a predetermined concentration is prepared. Incidentally, the float switch 33b is for detecting an abnormal water level and, thus, is not used in the ordinary operation.

Where the sterilization is performed by using warmed chemicals and the chemicals are discarded after use, it suffices to mix the concentrated solutions of the chemicals within the disinfecting solution tank 18 without diluting the disinfecting-sterilizing solution in advance. In other words, water need not be supplied into the disinfecting solution tank 18.

In this case, the concentrated disinfecting-sterilizing solution is supplied into the washing vessel 1 when the disinfecting-sterilizing operation is started, followed by supplying warm water into the washing vessel 1 so as to prepare the disinfecting-sterilizing solution. Incidentally, it is possible to supply the concentrated disinfecting-sterilizing chemicals from the bottles of the concentrated chemicals directly into the washing vessel 1.

Various forms of chemicals may be housed in the bottles 19 shown in FIGS. 2A to 2C. These chemicals may be in the form of, for example, a liquid, a powder or a solid. The chemicals used in the present invention produce a disinfecting capability (capability of killing harmful bacteria) at room temperature or a sterilizing capability (capability of killing all the bacteria) at room temperature. Alternatively, these chemicals produce a sterilizing capability when warmed. It follows that, where it suffices to obtain a disinfecting effect, the disinfection is performed at room temperature.

The concentrated chemicals are set in a predetermined upper portion within the bottle 19 so as to fall gravitationally into the disinfecting solution tank 18 when the electromagnetic valves 20a, 20b are turned on. Then, a button of the main panel is operated so as to introduce automatically city water or warm water into the disinfecting solution tank 18 so as to prepare a disinfecting-sterilizing solution of a practical concentration. It should be noted that the tubular passageway connected to the disinfecting solution tank 18 communicates with the washing vessel 1 via a pump 21.

A vapor component removing member 22 consisting of, for example, an activated carbon filter is mounted at the portion where the disinfecting-sterilizing solution communicates with the outside. Also, an alkali-based detergent or an enzyme-based detergent is housed in a detergent bottle 23. A tubular passageway connected to the detergent bottle 23 communicates with the washing vessel 1 via a pump 24. It should be noted that the alkali-based detergent or enzyme-based detergent serves to remove organic substances such as proteins and blood. On the other hand, the oxide-based disinfecting-sterilizing agent such as acetic peracid serves to remove inorganic substances such as calcium carbonate.

A drain pipe 28 is connected at one end to the waste water discharge port of the washing vessel 1 and extends to permit the other end to be positioned outside the apparatus via a drain pipe 29.

The apparatus of the first embodiment, which is constructed as described above, is operated as follows. Specifically, when the washing-disinfecting apparatus body is used, a used endoscope a is set within the washing vessel 1, and the tube 14 for washing the fluid passageway within the endoscope is connected at one end to the endoscope a and at the other end to the channel connecting port 13. Then, various switches (not shown) are operated to perform the steps of washing, disinfecting-sterilizing, rinsing, air blowing, etc. In the washing step, the water supply valve 31 is opened so as to supply washing water such as city water from the water supply source into the washing vessel 1 through the bacteria-removing filter 7 and the water supply tubular passageway. Also, the detergent supply pump 24 is operated to supply the detergent within the detergent bottle 23 into the washing vessel 1.

When the washing water supplied into the washing vessel 1 has reached a predetermined water level, the water supply valve 31 is closed so as to start the washing operation. In the washing step, an ultrasonic wave washing and the washing with the circulating washing water spurted from the spurting port are carried out independently or simultaneously.

Further, the pump 12 for washing the tubular passageway within the endoscope is operated so as to pressurize the washing solution within the washing vessel 1. As a result, the pressurized washing solution is supplied into all the tubular passageways within the endoscope 1. In this case, the pump operation is controlled to permit the flowing speed of the washing solution within at least the suction tubular passageway of the endoscope a to be at least 100 cm/sec.

A rinsing step is performed after completion of the washing step. Specifically, clean water is introduced into the washing vessel after discharge of the washing solution so as to carry out the rinsing operation once or twice. In the latter half of the rinsing operation, the pump 12 for washing the tubular passageway within the endoscope is stopped, and the compressor 17 is turned on. As a result, air is introduced through the channel connecting port 13 into various channels of the endoscope a so as to remove water from within the channels of the endoscope a.

Then, the disinfecting-sterilizing step is performed after completion of the rinsing step. In the disinfecting-sterilizing step, the oxide-based disinfecting-sterilizing agent within the disinfecting solution tank 18 is supplied into the washing vessel 1 through the disinfecting solution supply tubular passageway. As a result, the endoscope a is completely dipped in the disinfecting solution stored in the washing vessel 1. At the same time, the pump 12 for washing the tubular passageway of the endoscope is operated so as to supply the disinfecting-sterilizing solution within the washing vessel 1 into the tubular passageway of the endoscope so as to disinfect and sterilize the endoscope a.

The valve is opened a predetermined time later so as to recover the disinfecting-sterilizing solution in the disinfecting solution tank 18. The disinfecting-sterilizing solution thus recovered is used repeatedly as far as the solution produces the disinfecting-sterilizing effect.

After completion of the disinfecting-sterilizing step, the rinsing step is performed again.

After completion of the rinsing step, the water removing operation is carried out so as to remove water completely from within the endoscope a.

As described above, the apparatus for washing and disinfecting-sterilizing an endoscope according to the first embodiment of the present invention makes it possible to disinfect and sterilize the endoscope without fail in a short time so as to lessen markedly the burden of the user.

Figure 5:
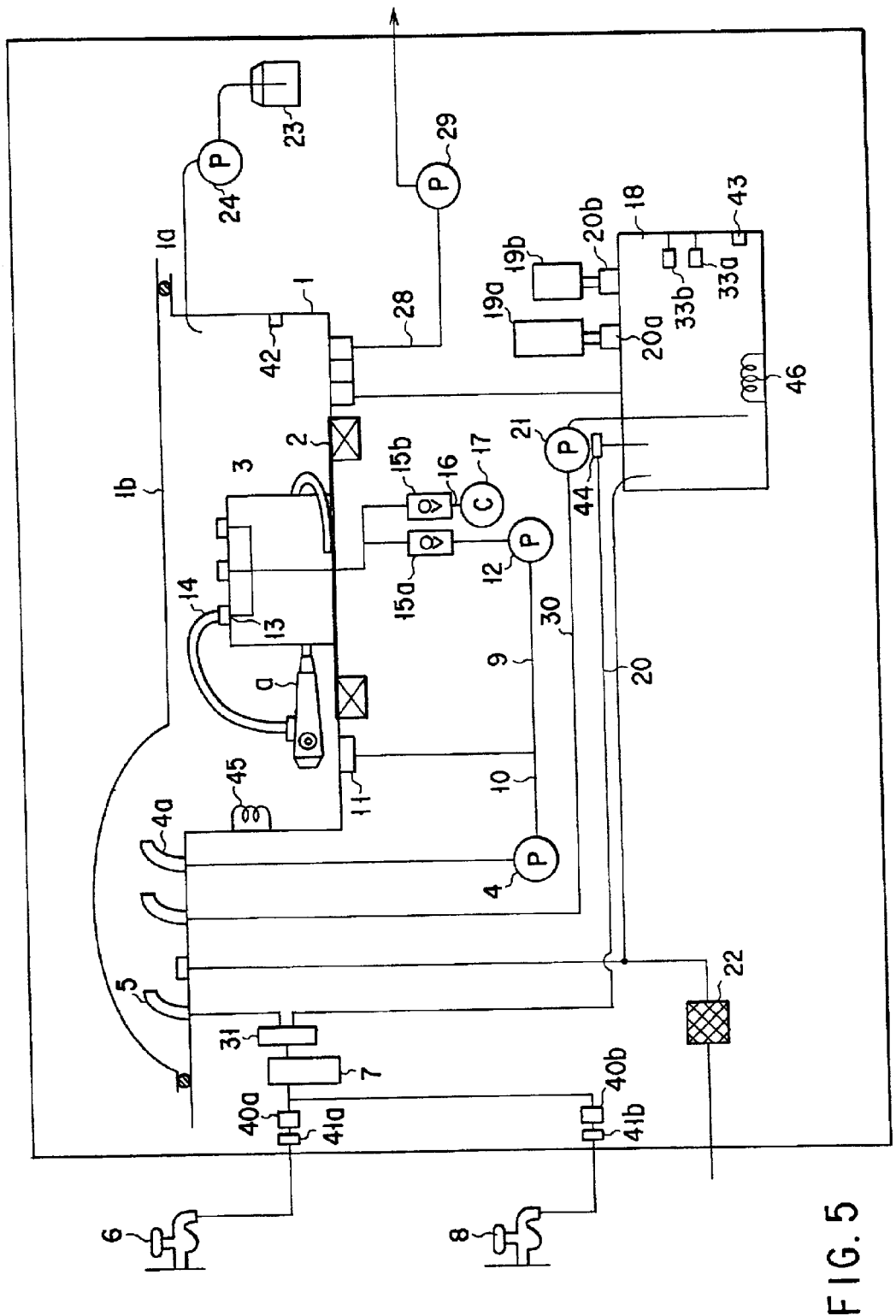
FIG. 5 shows the entire construction of an apparatus for washing and disinfecting-sterilizing an endoscope according to a second embodiment of the present invention.

FIG. 5 shows an apparatus according to a second embodiment of the present invention. Those members of the apparatus which are common with the members in the first and second embodiments are denoted by the same reference numerals so as to omit an overlapping description. In the apparatus of the second embodiment, the city water and a warm water from a warm water supply equipment can be supplied to the washing vessel 1 so as to prepare a disinfecting solution based on the warm water.

As shown in FIG. 5, a water supply valve 40a consisting of an electromagnetic valve is mounted o a tubular passageway connected to the water cock 6. Also, a warm water supply valve 40b consisting of an electromagnetic valve is mounted to the tubular passageway connected to a warm water supply equipment 8. These water supply valve 40a and the warm water supply valve 40b are connected to the control section C.

Temperature sensors 41a, 41b are mounted to the tubular passageways connected to the city water cock 6 and the warm water supply equipment 8, respectively. Also, temperature sensors 42, 43 are mounted to the washing vessel 1 and the disinfecting solution tank 18, respectively. Further, a flow meter 44 for measuring the water amount flowing into the disinfecting solution tank 18 is connected to the tubular passageway 20, which is connected at one end to the tank 18 and at the other end to the city water cock 6 and the warm water supply equipment 8.

Heaters 45 and 46 for heating the washing solution and the disinfecting-sterilizing solution housed in the washing vessel 1 and the disinfecting solution tank 18 are mounted within the washing vessel 1 and the tank 18, respectively. These temperature sensors 42, 43, flow meter 44 and heaters 45, 46 are connected to the control section C.

Incidentally, each of the disinfecting solution tank 18 and the washing vessel 1 is formed of a material resistant to chemicals and heat such as stainless steel, polyethylene or polypropylene.

The control section C, which is connected to the temperature sensors 41a, 41b, detects the temperature of the city water supplied from the city water cock 6 and the temperature of the warm water supplied from the warm water supply equipment 8.

If the temperature of the disinfecting solution is set by an operator in the control section C, the mixing ratio of the city water to the warm water is determined in the control section C based on the temperatures set for the disinfecting solution, for the city water and for the warm water supplied from the warm water supply equipment. Then, the required amounts of the city water and warm water are calculated based on the mixing ratio thus determined and the volume of the disinfecting solution tank 18.

In the next step, the control section C permits the water supply valve 40a to be opened based on the calculation so as to supply the city water. In this step, the supply amount of the city water is calculated on the basis of the indication of the flow meter 53. When a required amount of the city water has been supplied into the disinfecting solution tank 18, the city water supply valve 40a is closed so as to stop supplying the city water.

Then, the warm water supply valve 40b is opened so as to supply a warm water. In this step, the supply amount of the warm water is calculated on the basis of the indication of the flow meter 44. When a required amount of the warm water has been supplied into the disinfecting solution tank 18, the warm water supply valve 40b is closed so as to stop supplying the warm water. At the same time, the electromagnetic valves 20a, 20b are operated by the control section C so as to supply the concentrated disinfecting-sterilizing agent into the warm water within the disinfecting solution tank 18, thereby preparing a diluted disinfecting-sterilizing solution. During preparation of the diluted disinfecting-sterilizing solution, the heaters 45 and 46 within the washing vessel 1 and the disinfecting solution tank 18 are controlled by the control section C so as to maintain constant the temperature of the washing solution and the disinfecting-sterilizing solution, respectively. The apparatus of the second embodiment is equal to that of the first embodiment in the other respects.

The apparatus of the second embodiment permits disinfecting and sterilizing the endoscope without fail in a short time. In addition, the burden of the operator can be markedly lessened. It should be noted in particular that, in the apparatus of the second embodiment, a warm water equipment is arranged outside the apparatus body, making it unnecessary to prepare a warm water within the apparatus body. It follows that it suffices to use a small heater as far as the temperature of the disinfecting-sterilizing solution can be maintained at a predetermined level.

Figure 6A:
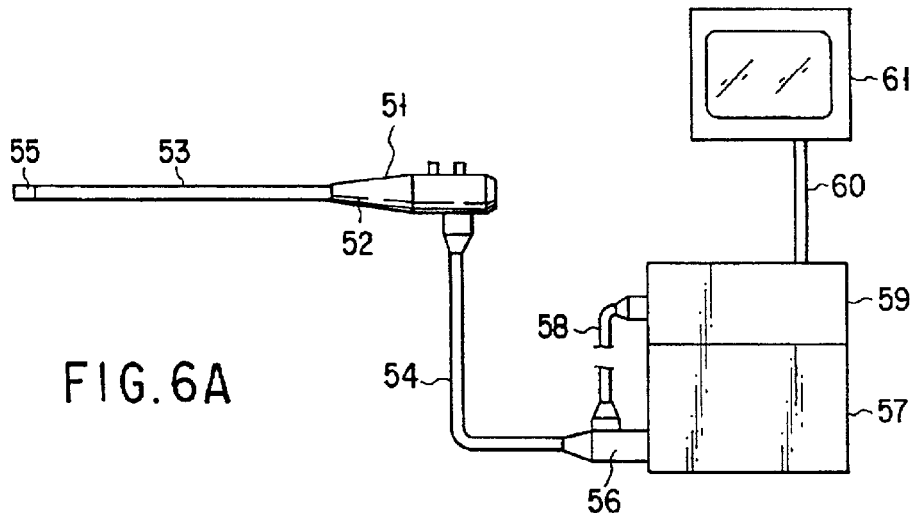
FIGS. 6A and 6B are oblique showing an endoscope apparatus and an apparatus for washing and disinfecting-sterilizing the endoscope according to a third embodiment of the present invention.
Figure 6B:
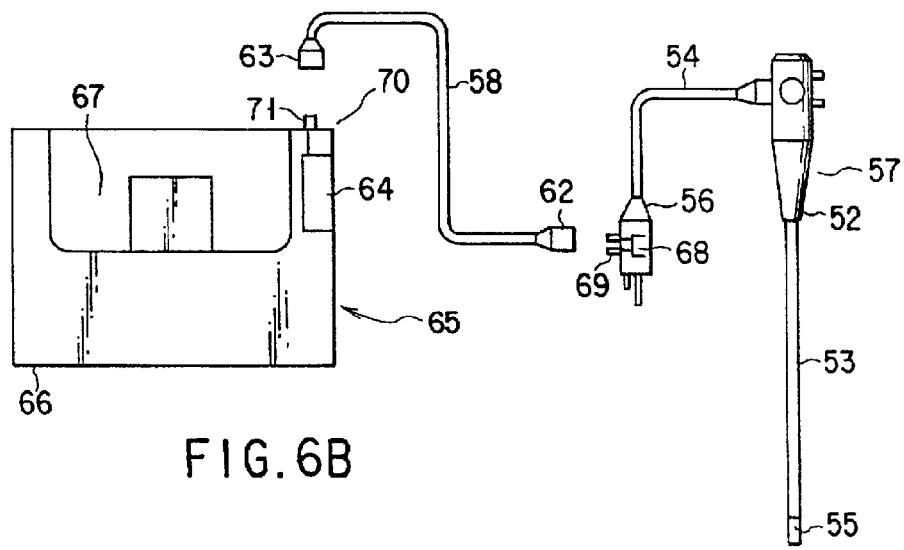
Figure 7:
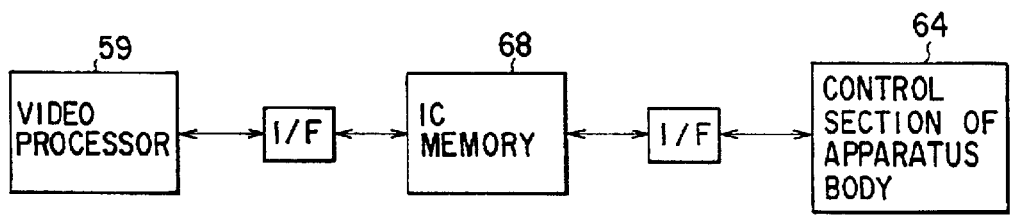
FIG. 7 is a block diagram showing the operation of the apparatus according to the third embodiment of the present invention.
Figure 8:
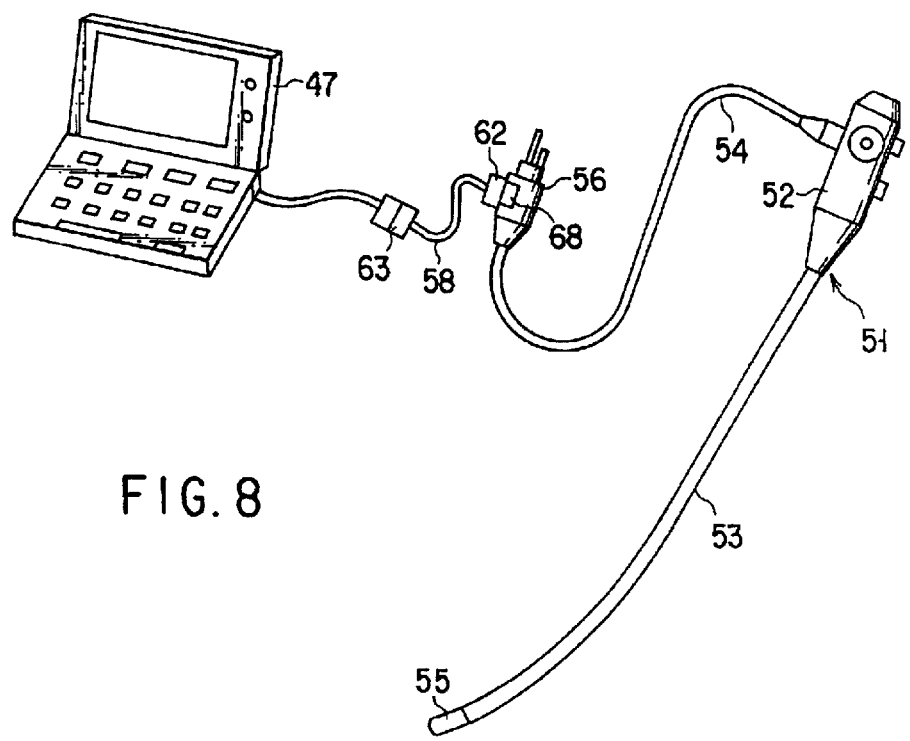
FIG. 8 is an oblique view showing data input state into an IC memory in the apparatus according to the third embodiment of the present invention.

FIGS. 6 to 8 show an apparatus according to a third embodiment of the present invention. Specifically, FIGS. 6A and 6B schematically show the construction of each of an endoscope apparatus and a washing-disinfecting-sterilizing apparatus. As shown in FIG. 6A, the endoscope apparatus comprises an endoscope 51 consisting of an operating section 52, an inserting section 53 and a universal cord 54. A solid camera element (not shown) such as a CCD is arranged within a distal end portion 55 of the inserting section 53. Also, a light guide cable (not shown) is inserted into the operating section 52 and into the inserting section 53. The light guide cable is connected at one end to an illuminating optical system arranged in the distal end portion 55 of the inserting section 53 and at the other end to a connector 56 via the universal cord 54.

The connector 56 is detachably connected to a light source device 57 included in the peripheral apparatus and is also connected to a video processor 59 via a signal cable 58. A video signal generated from the video processor 59 is supplied through an electric cable 60 to an observation monitor 61, with the result that the image observed by the endoscope is displayed on the monitor 61.

As shown in FIG. 6B, the signal cable 58 is connected at one end to a first connector 62 and at the other end to a second connector 63. It should be noted that signals generated from the endoscope 51 and the video processor 59 are exchanged.

In order to avoid, for example, infection, the outer surface and inner tubular passageway of the endoscope 51 must be washed and disinfected every time the endoscope 51 is used. An apparatus 65 for washing and disinfecting-sterilizing an endoscope comprises an apparatus body 66. A washing vessel 67 is included in the apparatus body 66. For performing the washing and disinfecting operation, the endoscope 51 is set within the washing vessel 67. To be more specific, the endoscope 51 after use is set in the washing vessel 67. Under this condition, various switches are operated so as to perform automatically the steps of washing, disinfecting-sterilizing, rinsing and air blowing based on instructions given by a control section 64.

An IC memory 68, which is mounted within the connector 56 of the endoscope 51, is electrically connected to a connecting terminal 69 projecting to the outside of the connector 56. Further, a control section 70 electrically connected to the control section 64 of the washing-disinfecting apparatus 65 is mounted to a part of the apparatus body 66. Also, a connecting terminal 71 is mounted to the connecting section 70.

The first connector 62 of the signal cable 58 is detachably connected to the connecting terminal 69 of the connector 56, and the second connector 63 is detachably connected to the connecting terminal 71 of the apparatus body 66 so as to permit exchange of signals between the endoscope 51 and the control section 64 of the apparatus body 66.

Various data of the endoscope 51 including the kinds, e.g., an endoscope for stomach, an endoscope for duodenum, an endoscope for large intestine and an endoscope for bronchia, date of manufacture, date of delivery, etc. are stored in an IC memory 68 arranged in the connector 56 of the endoscope 51 by connecting the second connector 63 of the signal cable 58 to a personal computer 47 and by connecting the first connector 62 of the signal cable 58 to the connector 56 of the endoscope 51, as shown in FIG. 8.

Where the endoscope 51 is used for inspection, various data such as the total number of inspections, date of inspection and the inspecting time are supplied from the video processor 59 to the IC memory 68 through the signal cable 58 so as to be stored in the IC memory 68, as shown in FIG. 6A.

In washing the endoscope 51 after the endoscopic inspection, the first connector 62 of the signal cable 58 is connected to the connection terminal 69 of the connector 56 included in the endoscope 51, and the second connector 63 of the signal cable 58 is connected to the connection terminal 71 of the apparatus body 66, as shown in FIG. 6B. As a result, the data stored in the IC memory 68 of the endoscope 51 are transferred to the control section 64 of the apparatus body 66. In other words, the data of the endoscope 51 including the kind, date of manufacture, date of delivery, the number of inspections, date of inspection and inspecting time, which are stored in the IC memory 68 of the endoscope 51, are transferred to the control section 64 of the apparatus body 66 by simply connecting the endoscope 51 to the apparatus body 66 by the signal cable 58. It follows that the treating time for any of the washing, disinfecting, and water removing steps can be determined within the apparatus body 66 depending on the kind of the endoscope 51. It is also possible for the apparatus body 66 to recognize the number of uses of the endoscope 51, the time from completion of the inspection to the washing-disinfecting step, etc., and to determine the washing-disinfecting conditions based on the result of the recognition.

The treating time for each of the washing, disinfecting and water removing steps depending on the kind of the endoscope 51 is as shown in, for example, Table 1.

TABLE 1

| Kind of Endoscope | Washing | Disinfecting | Water Removal |
|---|---|---|---|
| For stomach | 3 minutes | 20 minutes | 1 minute |
| For large intestine | 5 minutes | 20 minutes | 2 minutes |
| For Duodenum | 5 minutes | 30 minutes | 3 minutes |
| For Bronchia | 3 minutes | 45 minutes | 1 minute |

Scratches or the like given to the inserting section 53, etc. of the endoscope 51 are increased with increase in the number of inspections performed by the endoscope 51, with the result that the endoscope 51 tends to be stained easily and severely. Also, in the case where the washing treatment is performed a long time after completion of the inspection, stains tend to be attached firmly even to a new endoscope and are unlikely to be removed easily from the new endoscope. In the present invention, however, an appropriate treating time for any of the washing and disinfecting-sterilizing steps can be determined on the basis of the data stored in the IC memory 68.

Let us describe the function of the apparatus according to the third embodiment of the present invention.

For performing an endoscopic inspection, the connector 56 of the universal code 54 included in the endoscope 51 is connected to the light source device 57, and the connector 56 is also connected to the video processor 59 via the signal cable 58, as shown in FIGS. 6A and 7. Further, if the endoscopic inspection is performed by connecting the video processor 59 to the observation monitor 61 via the electric cable 60, various data including the date of inspection, the number of times of inspection, the inspecting time and, when the inspection is finished, the inspection finishing time are supplied from the video processor 59 to the IC memory 68 through an interface I/F. Incidentally, various data of the endoscope such as the kind, date of manufacture, date of delivery, and serial number are stored in the IC memory 68 when the endoscope is delivered to the user.

Upon completion of the endoscopic inspection, the connector 56 of the endoscope 51 is withdrawn from the light source device 57. Also, the second connector 63 of the signal cable 58 is withdrawn from the video processor 59. If the second connector 63 of the signal cable 58 is connected to the connection terminal 67 of the apparatus body 66 before the endoscope 51 is set in the washing vessel 67 of the washing-disinfecting apparatus 65, the data stored in the IC memory 68 of the endoscope 51 are supplied to the control section 64 of the apparatus body 66 via an interface I/F, as shown in FIGS. 6B and 7.

As described above, various data of the endoscope 51 such as the date of manufacture, the date of delivery, the number of times of inspection, the date of inspection and the inspection finishing time are stored in the control section 64 of the apparatus 65 for washing and disinfecting-sterilizing an endoscope. As a result, the treating time for each of the washing, disinfecting-sterilizing and water removing steps can be set within the apparatus body 66 depending on the kind of the endoscope 51. It is also possible for the apparatus body 66 to recognize the number of uses of the endoscope 51, the time from completion of the inspection to the washing-disinfecting step, etc., and to determine automatically the washing-disinfecting conditions based on the result of the recognition. Naturally, the endoscope 51 is subjected to the washing, disinfecting-sterilizing and water removing treatments in accordance with the conditions thus set.

Since the conditions such as the time for any of the washing, disinfecting-sterilizing and water removing steps are determined on the basis of the data such as the kind of the endoscope 51, the number of uses of the endoscope 51 and the time from completion of inspection to the washing, adverse effects given to the endoscope 51 by the insufficient washing or excessive washing can be prevented, making it possible to carry out the washing and disinfecting-sterilizing treatments adapted for the individual endoscope 51. Incidentally, it is also possible to set the temperature of the washing solution and to change appropriately the amount and kind of the detergent and the disinfecting-sterilizing agent while setting the time for each of the washing and disinfecting-sterilizing treatments.

Figure 9A:
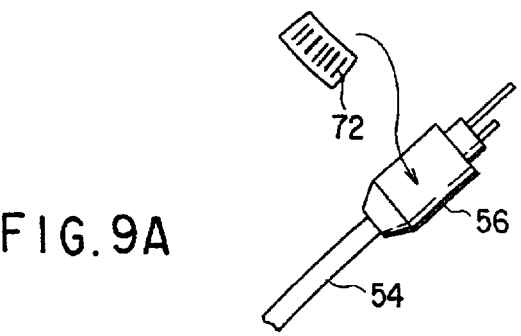
FIGS. 9A and 9B are oblique views collectively showing an apparatus for washing and disinfecting-sterilizing an endoscope according to a fourth embodiment of the present invention.
Figure 9B:
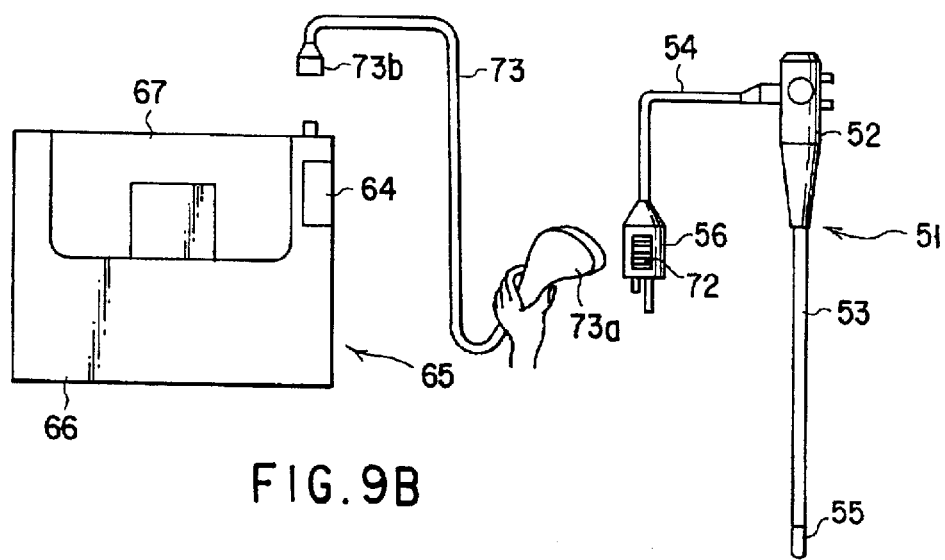
Figure 10:
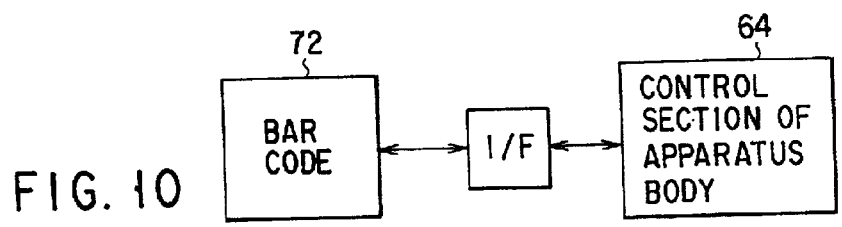
FIG. 10 is a block diagram showing the operation of the apparatus according to the fourth embodiment of the present invention.

FIGS. 9A, 9B and 10 collectively show an apparatus according to a fourth embodiment of the present invention.

Those members of the apparatus of the fourth embodiment which are common with the members of the third embodiment are denoted by the same reference numerals so as to omit description thereof in the following description. In the apparatus of the fourth embodiment, a bar code 72 is attached to the connector 56 of the endoscope 51 and a bar code reader 73a is mounted to the signal cable 73 as shown in FIG. 9A in place of using the IC memory 68 used in the third embodiment. Various data of the endoscope such as the kind, date of manufacture, date of delivery and serial number are recorded in the bar code 72 in the step of delivering the endoscope to the user.

Before the endoscope 51 is set in the washing vessel 67 of the apparatus 65 for washing and disinfecting the endoscope 51 after completion of the endoscopic inspection, the connector 73b of a signal cable 73 is connected to the connection terminal 67 of the apparatus body 66 so as to permit the bar code reader 73a to read the bar code 72 attached to the connector 56 as shown in FIG. 9B. As a result, the data recorded in the bar code 72 are transmitted to the control section 64 of the apparatus body 66 through the I/F.

As described above, the data of the endoscope 51 such as the kind, date of manufacture and date of delivery are stored in the control section 64 of the apparatus 65 for washing and disinfecting-sterilizing the endoscope. Therefore, the time for each of the washing, disinfecting-sterilizing and water removing steps is set within the apparatus body 66 depending on the kind of the endoscope 51. It is also possible for the apparatus body 66 to recognize the time from the date of manufacture of the endoscope 51 and to set automatically the washing-disinfecting conditions based on the result of the recognition. Naturally, the washing, disinfecting-sterilizing and water removing steps can be applied to the endoscope 51 in accordance with the conditions thus set.

Since the conditions such as the time for any of the washing, disinfecting-sterilizing and water removing steps are determined on the basis of the data such as the kind of the endoscope 51 and the time from the date of manufacture, adverse effects given to the endoscope 51 by the insufficient washing or excessive washing can be prevented, making it possible to carry out the washing and disinfecting-sterilizing treatments adapted for the individual endoscope 51. Incidentally, it is also possible to set the temperature of the washing solution and to change appropriately the amount and kind of the detergent and the disinfecting-sterilizing agent while setting the time for each of the washing and disinfecting-sterilizing treatments.

Figure 11:
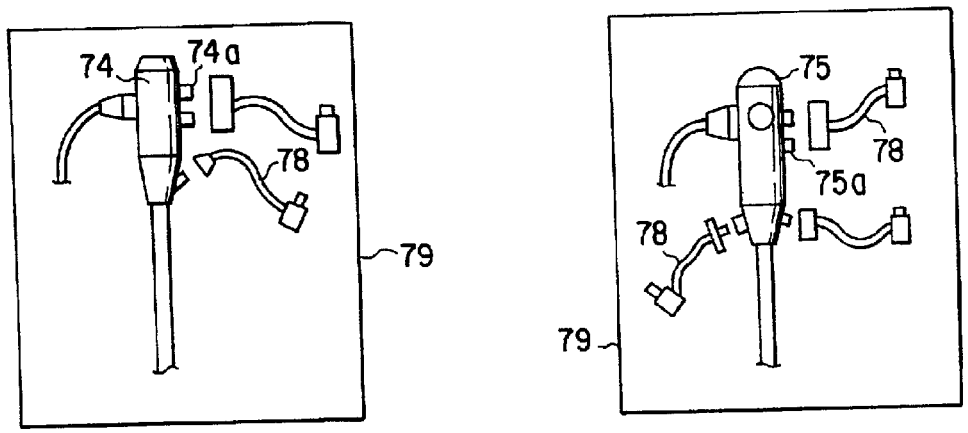
FIG. 11 shows the construction of an apparatus for washing and disinfecting-sterilizing an endoscope according to a fifth embodiment of the present invention.
Figure 11:
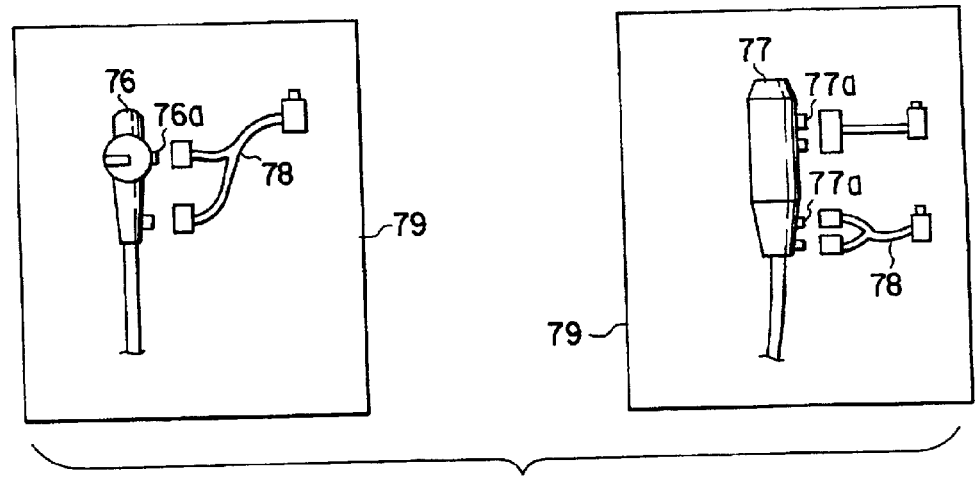

FIG. 11 shows an apparatus according to a fifth embodiment of the present invention. As described previously, endoscopes includes various types such as an endoscope 74 for stomach, an endoscope 75 for duodenum, an endoscope 76 for large intestine, and an endoscope 77 for bronchia. These endoscopes differ from each other in the arrangement of the internal tubular passageways and the number of bases 74a, 75a, 76a, 77a. Therefore, it is necessary to connect without fail a tube 78 used exclusively for washing the tubular passageway to any of the bases 74a, 75a, 76a, 77a communicating with the internal tubular passageways of the endoscope.

In the fifth embodiment of the present invention, a display section 79 is mounted to the apparatus body 66 of the washing-disinfecting apparatus 65 in addition to the constituents of the apparatus according to the third or fourth embodiment. An image of the tube 78 for washing the tubular passageway is displayed in the display section 79 together with images of the endoscope 74 for stomach, endoscope 75 for duodenum, endoscope 76 for large intestine and endoscope 77 for bronchia so as to permit the tube 78 for washing the tubular passageway to be connected without fail to the base 74a, 75a, 76a or 77a before application of the washing-disinfecting treatment to the endoscope. It follows that the tubular passageways are washed without fail.

In any of the third to fifth embodiments described above, the washing-disinfecting treatment can be performed appropriately to meet the requirement of the endoscope, making it possible to prevent the insufficient washing or excessive washing of the endoscope.

Figure 12:
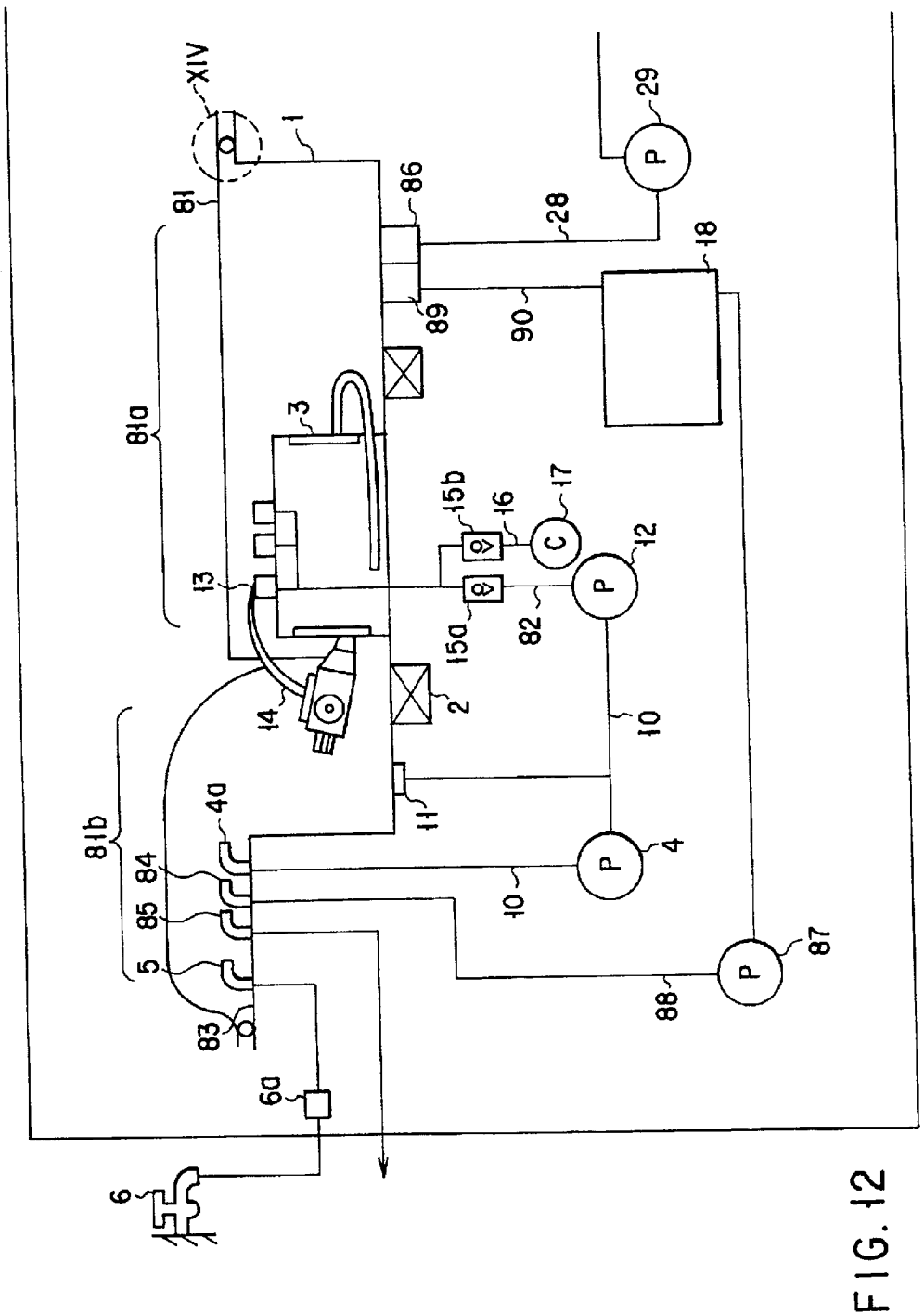
FIG. 12 shows the construction of an apparatus for washing and disinfecting-sterilizing an endoscope according to a sixth embodiment of the present invention.

FIGS. 12 to 14 show an apparatus according to a sixth embodiment of the present invention. Those members of the apparatus of the sixth embodiment which are common with the members of the apparatus of the first embodiment are denoted by the same reference numerals so as to omit the overlapping description.

As shown in FIG. 12, a top cover 81, which forms the ceiling of the washing vessel 1 and which can be opened, is mounted to close partially the upper opening of the washing vessel 1 having the endoscope a disposed therein. The top cover 81 is opened when the endoscope a is set in the washing vessel 1.

A nozzle-mounting table 83 is formed in a part of the upper peripheral portion of the washing vessel 1. Various nozzles such as a washing solution nozzle 4a, a washing water nozzle 5, a disinfecting solution nozzle 84 and an air-release nozzle 85 are mounted to the nozzle-mounting table 83. In order to prevent the washing water or the disinfecting solution from flowing backward out of the washing vessel 1, these nozzles must be mounted at a position higher than the liquid level within the washing vessel 1. To meet this requirement, the nozzle-mounting table 83 having a reasonable height is formed in a part of the washing vessel 1, and the nozzles are mounted to the table 83.

As shown in FIG. 13, the disinfecting solution nozzle 84 consists of a pipe bent in an inverted J-shape and includes a slit 84a formed in the upper portion of the bent pipe such that the disinfecting-sterilizing agent is partly spurted upward from the slit 84a.

The nozzle 4a for the washing solution is connected to the discharge port of the washing solution pump 4 via the tubular passageway 10. On the other hand, the suction port of the pump 4 is connected to the circulating solution suction port 11 formed at a bottom portion of the washing vessel 1. Also, the channel connection port 13 connected to the tube 14 for washing the tubular passageway within the endoscope is formed in a tower 3 arranged within the washing vessel 1. Further, a discharge port 86 is formed in a bottom portion of the washing vessel 1.

The disinfecting solution tank 18 is connected to the disinfecting solution nozzle 84 via a tubular passageway 88 having a pump 87 mounted thereto. The disinfecting-sterilizing agent stored in the tank 18 is supplied into the washing vessel 1 by the sucking function of the pump 87. Also, a tubular passageway 90 for circulating the disinfecting solution and the tubular passageway 28 for the waste solution are connected to a tubular passageway extending from the discharge port 86 with a tubular passageway change-over switch 89 interposed therebetween. The tubular passageway 90 is connected to the disinfecting solution tank 18 so as to recover the disinfecting-sterilizing agent from the washing vessel 1 into the disinfecting solution tank 18.

The top cover 81 covering the open portion of the washing vessel 1 comprises a planar portion 81a contacting the liquid surface when the washing vessel 1 is filled with the washing solution or the disinfecting-sterilizing agent and a projecting portion 81b covering the nozzles 4a, 5, 84, 85 mounted to the nozzle-mounting table 83 and positioned higher than the liquid surface. The top cover 81 is swingably mounted to an upper peripheral portion of the washing vessel 1 by a hinge (not shown) such that the top cover 81 can be opened or closed.

Further, a horizontal supporting portion 1c for supporting an outer peripheral portion 81c of the top cover 81 is formed on the upper peripheral portion 1b of the washing vessel 1, as shown in FIG. 14. Also, a rising portion 1d is formed to project upward from the outer circumferential portion of the supporting portion 1c. Further, a packing 91 is interposed between the outer peripheral portion 81c of the top cover 81 and the horizontal supporting portion 1c so as to keep the washing vessel 1 liquid-tight. It should be noted that the top cover 81 is locked to the washing vessel 1 by a clamp mechanism (not shown).

Let us describe the function of the apparatus according to the sixth embodiment of the present invention. In the first step, a used endoscope a is set in the washing vessel 1, and the endoscope a is connected to the channel connection port 13 via the tube 14 for washing the tubular passageway of the endoscope. Then, the top cover 81 is closed to make the washing vessel 1 completely liquid-tight, followed by operating the various switches (not shown) so as to perform automatically the steps of washing, disinfecting-sterilizing, rinsing and air-blowing.

In the washing step, the water supply valve 6a is opened to supply the washing water from the city water cock 6 into the washing vessel 1 through the washing water nozzle 5. Incidentally, a predetermined amount of a detergent is supplied into the washing vessel 1 before the washing step.

When a predetermined amount of water is supplied into the washing vessel 1, the water supply valve 6a is closed, followed by driving the pump 4 for circulating the washing water and the pump 12 for washing the tubular passageways of the endoscope. As a result, the washing water within the washing vessel 1 is partly blown at a high pressure against the outer surface of the endoscope a and circulated through the washing water tubular passageway 82 into the tubular passageways of the endoscope a. To be more specific, the washing water within the washing vessel 1 is sucked through the suction port 11 of the circulating water by the function of the pump 4 so as to be spurted from the washing water spurting nozzle 4a through the washing water tubular passageway 10. Also, the washing water sucked by the function of the pump 4 is sucked partly by the function of the pump 12 so as to be supplied to the channel connection port 13 through the tubular passageway 82. Then, the washing water is supplied from the channel connection port 13 into the tubular passageways within the endoscope a. It should be noted that the washing water supplied into the tubular passageways within the endoscope a is brought back into the washing vessel 1 through an opening at the distal end of the endoscope a.

The large stains, soft stains and light stains attached to the endoscope a are washed away by the circulation of the washing water described above. Particularly, these stains are peeled off the outer surface of the endoscope a by the impact of the washing water spurted from the washing water nozzle 4a or by the eddy current formed within the washing vessel 1 by the spurting of the washing water noted above.

After the washing with the washing water, which is continued for a predetermined time, the vibrating plate 2 is operated so as to carry out an ultrasonic washing. In the ultrasonic washing, the stains firmly attached to the endoscope a and the stains attached to those portions of the endoscope a which are shaped complex are removed by the ultrasonic vibration oscillated from the vibrating plate 2.

After completion of the ultrasonic washing, the endoscope a is washed again by the circulating washing water. In this step, the stains swollen by the ultrasonic washing so as to be attached only lightly to the endoscope a are removed by the circulating washing water.

After completion of the washing step, the rinsing step is carried out. In the rinsing step, driving of the pumps 4 and 12 is stopped first. Then, the waste water pump 29 is driven, and the tubular passageway change-over valve is switched to open the waste water tubular passageway 28. As a result, the washing liquid within the washing vessel 1 is discharged from the disport 86 to the outside through the tubular passageway 28 for the waste water. When the washing water within the washing vessel 1 is discharged completely, the water supply valve 6a is opened so as to supply a rinsing water into the washing vessel 1. Then, the pumps 4 and 12 are driven again so as to permit the rinsing water to be circulated, with the result that the inner tubular passageways and the outer surface of the endoscope a are rinsed.

After completion of the rinsing step, the rinsing water is discharged completely from within the washing vessel 1. Under this condition, water remaining inside the endoscope a is removed. In this water removing step, driving of the pumps 4 and 12 is stopped. Also, the compressor 17 is driven to blow air into the tubular passageway 82 through the air supply tubular passageway 16. The air blown into the tubular passageway 82 is supplied into the tubular passageways within the endoscope a so as to remove water remaining inside the inner tubular passageways of the endoscope a.

After completion of the rinsing step, the disinfecting-sterilizing step is performed. In this disinfecting-sterilizing step, the pump 87 is driven first. As a result, the disinfecting solution within the disinfecting solution tank 18 is supplied into the tubular passageway 88 so as to be poured into the washing vessel 1 through the disinfecting solution nozzle 84. The disinfecting solution is poured into the washing vessel 1 until the washing vessel 1 is filled with the disinfecting-sterilizing solution. Naturally, the planar portion 81a of the top cover 81 is in contact with the disinfecting-sterilizing solution filling the washing vessel 1.

As described previously, the slit 84a is formed in the disinfecting solution nozzle 84, with the result that the disinfecting-sterilizing solution is spurted partly from the slit 84a toward the inner surface of the projecting portion 81b of the top cover 81 so as to disinfect-sterilize the inner surface of, particularly, the projecting portion 81b of the top cover 81. When a predetermined amount of the disinfecting-sterilizing solution is poured into the washing vessel 1 to permit the endoscope a to be dipped completely within the disinfecting-sterilizing solution, driving of the pump 87 is stopped, followed by driving the pump 12 for the washing operation. As a result, the disinfecting-sterilizing solution within the washing vessel 1 is supplied into the inner tubular passageways of the endoscope a so as to disinfect-sterilize the inner tubular passageways of the endoscope a together with the side wall of the washing vessel 1 and the inner surface of the top cover 81.

After the disinfecting-sterilizing step, which is continued for a predetermined time, the tubular passageway change-over valve 89 is switched to open the tubular passageway 90 so as to permit the disinfecting-sterilizing solution to be recovered in the disinfecting solution tank 18. Then, the rising step described previously is repeated so as to rinse the disinfecting solution.

After the disinfecting-sterilizing agent is completely removed by the rinsing step, the air blowing step is carried out. The air blowing step is performed like the water removing step performed in the latter part of the rinsing step described previously. Then, driving of the waste water discharge pump 29 is stopped a predetermined time later.

As described above, in the endoscope washing-disinfecting apparatus according to the sixth embodiment of the present invention, the washing vessel 1 is filled with the disinfecting-sterilizing solution in the disinfecting-sterilizing step such that the inner surface of the planar portion 81a of the top cover 81 is in contact with the disinfecting-sterilizing solution. Naturally, the inner surface of the planar portion 81a is disinfected with the solution. Also, the disinfecting-sterilizing solution is partly spurted through the slit 84a of the disinfecting solution nozzle 84, with the result that the inner surface of the projecting portion 81b of the top cover 81 is also disinfected and sterilized with the solution. In short, in the step of disinfecting the endoscope a, the side wall of the washing vessel 1 and the top cover 81 are also disinfected and sterilized simultaneously without fail.

What should be noted in particular is that the top cover 81 of the washing vessel 1 can be kept clean in the endoscope washing-disinfecting apparatus according to the sixth embodiment of the present invention, thereby to eliminate the possibility that the contaminants such as bacteria, which are attached to the wall of the washing vessel 1 and the inner surface of the top cover 81, are attached again to the endoscope a set in the washing vessel 1 so as to contaminate again the endoscope a.

In the sixth embodiment described above, the washing vessel 1 is filled completely with the disinfecting-sterilizing solution in the disinfecting-sterilizing step, and the disinfecting-sterilizing solution is spurted from the slit 84a. The particular technical idea can also be applied to the washing and rinsing steps. Specifically, it is possible to fill completely the washing vessel 1 with the washing solution and to permit the washing solution to be spurted from the washing solution nozzle 4a toward the projecting portion 81b of the top cover 81.

FIGS. 15A to 15D show modifications of the apparatus according to the sixth embodiment of the present invention. In the modification shown in FIG. 15A, a plurality of slits 84a are formed in the disinfecting solution nozzle 84 to permit the disinfecting solution to be spurted from these slits 84a in a plurality of different directions. In the modification shown in FIG. 15B, a spurting nozzle 84b is mounted to the disinfecting solution nozzle 84. In the modification shown in FIG. 15C, a spurting port 92 is formed in the tubular passageway 88 for the disinfecting solution or in the tubular passageway 10 for the washing solution. Further, in the modification shown in FIG. 15D, a disinfecting solution nozzle 93 is formed to face obliquely upward to permit the disinfecting-sterilizing solution to be spurted onto the top cover 81 and, at the same time, to be supplied into the washing vessel 1.

FIG. 16 shows an apparatus according to a seventh embodiment of the present invention. Those members of the apparatus which are common with the members of the apparatus of the sixth embodiment are denoted by the same reference numerals so as to avoid an overlapping description. In the apparatus of the seventh embodiment, an arcuate disinfecting solution nozzle 94 is mounted to the nozzle-mounting table 83 arranged within the washing vessel 1. In this embodiment, the washing vessel 1 is not completely filled with the disinfecting solution, with the result that the inner surface of the top cover 81 is not in direct contact with the disinfecting solution housed in the washing vessel 1. However, the surface region of the disinfecting solution is waved by operating a pump (not shown) so as to bring the disinfecting solution into contact with the inner surface of the top cover 81.

FIG. 17 shows an apparatus according to an eighth embodiment of the present invention. Those members of the apparatus which are common with the members of the apparatus of the sixth embodiment are denoted by the same reference numerals so as to avoid an overlapping description. In the apparatus of the eighth embodiment, the disinfecting-sterilizing solution filling the washing vessel 1 is in contact with the inner surface of the planar portion 81a of the top cover 81, with the result that the inner surface of the planar portion 81a is disinfected and sterilized. Also, a disinfecting solution nozzle 95 is mounted to the tower 3 arranged within the washing vessel 1, and the top cover 81 includes a projecting portion 81b positioned to face the tower 3. Further, a slit 95a for spurting the disinfecting-sterilizing solution to the projecting portion 81b is formed in the disinfecting solution nozzle 95, with the result that the projecting portion 81b of the top cover 81 is also disinfected and sterilized by the solution spurted from the slit 95a.

Figure 18:
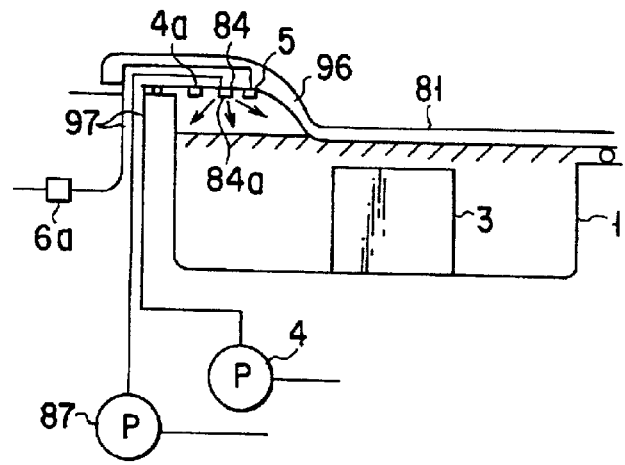
FIG. 18 shows the construction of an apparatus for washing and disinfecting-sterilizing an endoscope according to a ninth embodiment of the present invention.

FIG. 18 shows an apparatus according to a ninth embodiment of the present invention. Those members of the apparatus which are common with the members of the apparatus of the sixth embodiment are denoted by the same reference numerals so as to avoid an overlapping description. In the apparatus of the ninth embodiment, the inner surface of the planar portion 81a of the top cover 81 is in contact with the disinfecting-sterilizing solution filling the washing vessel 1, with the result that the inner surface of the planar portion 81a is disinfected and sterilized by the solution. Also, the top cover 81 is of a double-layer structure having an inner free space 96. Various tubular passageways 97 having a flexibility are arranged in the free space 96. The washing water nozzle 5, the washing solution nozzle 4a and the disinfecting solution nozzle 84, which are connected to the various tubular passageways 97, are mounted to face downward to the inner surface of the projecting portion 81b of the top cover 81. Also, a slit 84a for spurting the disinfecting-sterilizing solution toward the projecting portion 81b of the top cover 81 is formed in the side wall of the disinfecting solution nozzle 84, with the result that the projecting portion 81b is also disinfected and sterilized by the solution spurted from the slit 84a.

Figure 19A:
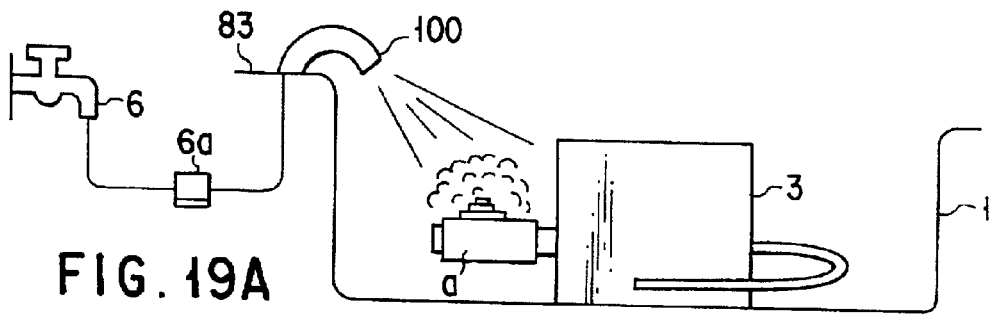
FIGS. 19A to 19C collectively show the construction of an apparatus for washing and disinfecting-sterilizing an endoscope according to a tenth embodiment of the present invention.
Figure 19B:
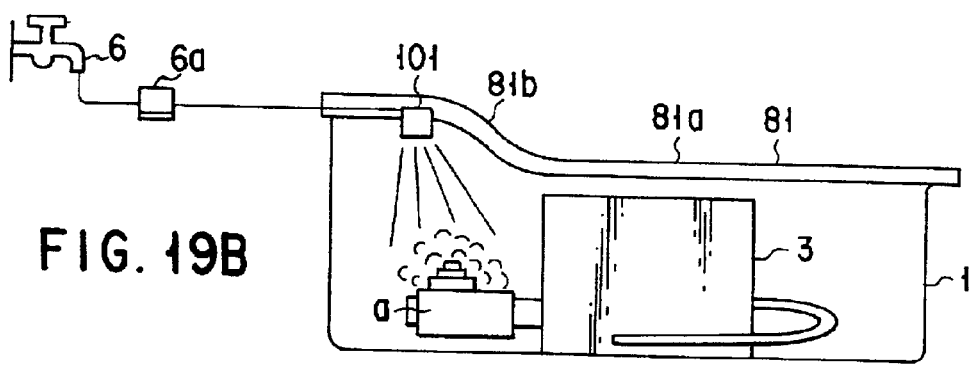
Figure 19C:
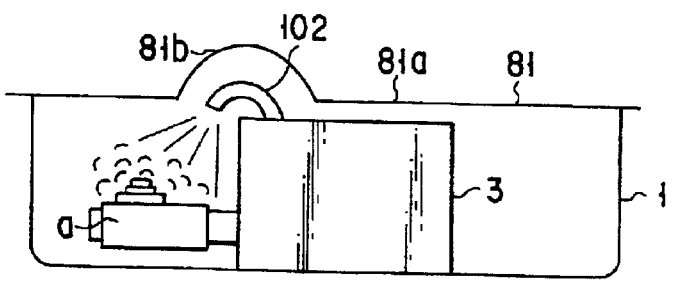

FIGS. 19A to 19C show an apparatus according to a tenth embodiment of the present invention. Those members of the apparatus which are common with the members of the apparatus of the sixth embodiment are denoted by the same reference numerals so as to avoid an overlapping description. It should be noted that, since the operating section of the endoscope a is complex in construction, the foam of the detergent used in the washing step is attached to small clearances in the operating section, leading to requirement of a long rinsing time. The tenth embodiment is intended to overcome this difficulty.

Specifically, FIG. 19A shows that a washing solution nozzle 100 for spurting the washing solution toward the operating section of the endoscope a is mounted to the nozzle-mounting table 83. FIG. 19B shows that a washing solution nozzle 101 for spurting the washing solution toward the operating section of the endoscope a is mounted to the inner surface of the projecting portion 81b of the top cover 81. Further, FIG. 19C shows that a washing solution nozzle 102 for spurting the washing solution toward the operating section of the endoscope a is mounted to the tower 3 arranged within the washing vessel 1. In the tenth embodiment, the washing solution is vigorously spurted to the operating section of the endoscope a so as to remove the foam of the detergent attached to the operating section in a short time. It follows that the rinsing step can be performed efficiently.

Figure 20:
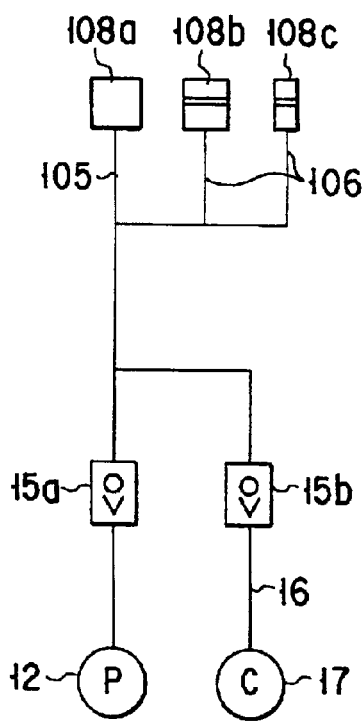
FIG. 20 shows the construction of a channel connector included in an apparatus according to an eleventh embodiment of the present invention.

FIG. 20 shows an apparatus according to an eleventh embodiment of the present invention. Those members of the apparatus which are common with the apparatus of the sixth embodiment are denoted by the same reference numerals so as to avoid an overlapping description. The apparatus of the eleventh embodiment comprises a first connector 108a, a second connector 108b and a third connector 108c. The first connector 108a, which is mounted to the tower 3 within the washing vessel and connected to a first branched tubular passageway 105, is normally kept open. On the other hand, the second and third connectors 108b and 108c, which are connected to a second branched tubular passageway 106, are normally kept closed. It follows that fluid flows through the first connector 108a, even if the tube 14 for washing the tubular passageways of the endoscope is not connected to the endoscope a. On the other hand, the second and third connectors 108b, 108c are closed when the tube 14 for washing the tubular passageways of the endoscope is not connected to the endoscope a, and permit fluid to flow through these second and third connectors 108b, 108c only when the tube 14 for washing the tubular passageways of the endoscope is connected to the endoscope a. The particular construction produces a prominent effect. Specifically, in washing an endoscope a which does not include inner tubular passageways such as a forceps channel and a suction tubular passageway, the tube 14 for washing the tubular passageways of the endoscope is not connected to the endoscope a, quite naturally. It follows that the flow amount of the fluid can be decreased. Also, a costly relief valve can be omitted, and the burden of the pump can be decreased.

Figure 21:
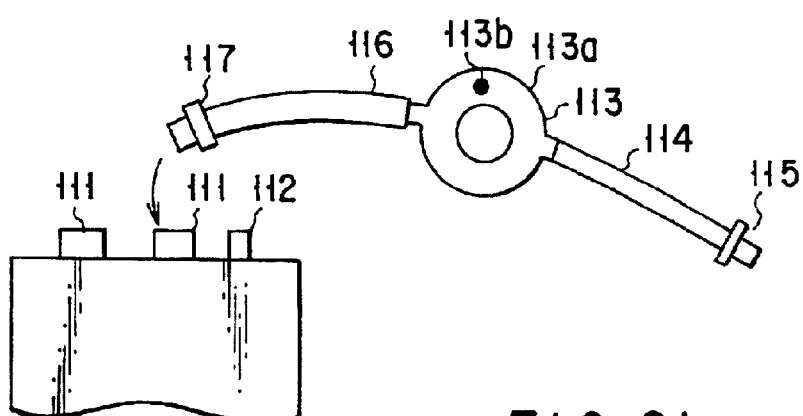
FIG. 21 shows a detector for detecting an abnormality of a tubular passageway, etc. included in an apparatus for washing and disinfecting-sterilizing an endoscope.

FIG. 21 shows a flow detector 113 for detecting whether or not the endoscope washing-disinfecting apparatus operates normally. The washing-disinfecting apparatus includes a large number of tubular passageways. Since it is naturally possible to use the apparatus for washing-disinfecting the endoscope a without knowing that the tubular passageway is plugged, it is necessary to check the apparatus before the washing-disinfecting operation. For performing the checking, a detector is connected to a connector for connecting the tube 14 for washing the tubular passageway of the endoscope so as to detect whether or not fluid actually flows out of the connector. In general, the washing-disinfecting apparatus comprises a connector 111 having a large diameter and a connector 112 having a small diameter. On the other hand, a connecting port 115 of a small diameter is connected to one end of the flow detector 113 via a tube 114. Also, a connecting port 117 having a large diameter is connected to the other end of the flow detector 113 via a tube 116. As shown in the drawing, the flow detector 113 comprises an annular passageway 113a having a ball 113b put therein. The ball 113b is circulated within the annular passageway 113a by the flow of fluid within the flow detector 113.

If the large diameter connecting port 117 of the flow detector 113 is connected to the large diameter connector 111 of the washing-disinfecting apparatus, the fluid flowing out of the large diameter connector 111 flows through the flow detector 113 so as to be discharged to the outside through the small diameter connecting port 115. Naturally, the ball 113b put in the flow detector 113 is rotated, if the fluid flows through the flow detector 113. In other words, movement of the ball 113b indicates that the washing-disinfecting apparatus operates normally. If the fluid does not flow through the flow detector 113, however, the ball 113b is kept stationary, indicating that the tubular passageway of the washing-disinfecting apparatus is plugged or the pump included in the washing-disinfecting apparatus fails to operate normally. Incidentally, it is also possible to connect the small diameter connecting port 115 of the flow detector 113 to the small diameter connector 112 of the washing-disinfecting apparatus, with the large diameter connecting port 117 allowed to act as a fluid discharge port.

The apparatus according to any of the sixth to eleventh embodiments of the present invention permits washing-disinfecting the endoscope and the washing vessel included in the washing-disinfecting apparatus without fail. Also, it is possible to prevent the endoscope after the washing-disinfecting treatment from being contaminated when the endoscope is taken out of the apparatus. It follows that infection of a disease via the endoscope can be prevented. Further, the washing-disinfecting apparatus can be simplified in construction and can also be miniaturized.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope washing and disinfecting apparatus, comprising:

a washing vessel configured to contain an endoscope, and having a depth such that the endoscope is immersible in a predetermined solution filled in the washing vessel;

an openable and closable cover provided at an upper section of the washing vessel for covering an opening of the washing vessel;

a first inner surface provided on the cover and set at a height such that the first inner surface is not brought into contact with an upper surface of the solution when the cover is closed and the endoscope is immersed in the solution filled in the washing vessel;

a second inner surface provided on the cover and set at a height such that the second inner surface is brought into contact with the upper surface of the solution when the cover is closed and the endoscope is immersed in the solution filled in the washing vessel; and a supply outlet configured to supply the solution to the washing vessel, and provided at a position that is: (i) higher than the upper surface of the solution when the endoscope is immersed in the solution filled in the washing vessel so as not to be brought into contact with the upper surface of the solution filled in the washing vessel, and (ii) lower than the first inner surface.

2. An apparatus according to claim 1, wherein said supply outlet is covered by the first inner surface of said cover when said cover is closed, and the first inner surface of said cover has a portion that covers said supply outlet at a position higher than the upper surface of the solution filled in said washing vessel.

3. An apparatus according to claim 2, wherein said washing vessel has a cover spray outlet configured to spray the same solution as the solution filled in said washing vessel towards the first inner surface of said cover that covers said supply outlet, said cover spray outlet being provided in the upper portion of said washing vessel at a position higher than the upper surface of the solution when the endoscope is immersed in the solution filled in said washing vessel.

4. An apparatus according to claim 3, wherein said cover spray outlet is formed on said supply outlet.

5. An apparatus according to claim 1, wherein a height of an outer peripheral portion of said cover and a height of a supporting portion of said washing vessel that supports the outer peripheral portion of said cover are set to a level of the upper surface of the solution when said cover is closed and the endoscope is immersed in the solution filled in said washing vessel, and wherein a packing is provided between the outer peripheral portion of said cover and the supporting portion of said washing vessel.

6. An apparatus according to claim 5, wherein a rising portion taller than the packing is provided at a position corresponding to an outer periphery of the packing.

7. An endoscope washing and disinfecting apparatus, comprising:

a washing vessel configured to contain an endoscope, and having a depth such that the endoscope is immersible in a predetermined solution filled in the washing vessel;

an openable and closable cover provided at an upper section of the washing vessel for covering an opening of the washing vessel; and a jet nozzle for discharging a jet of the same solution that is filled in the washing vessel at the solution filled in the washing vessel so as to vibrate an upper surface of the solution when the cover is closed and the endoscope contained in the washing vessel is immersed in the solution filled therein, and while the endoscope is cleaned by a circulating effect of the solution;

wherein the cover has an inner surface set at a height such that when the cover is closed and the endoscope contained in the washing vessel is immersed in the solution filled therein, the inner surface of the cover is not brought into contact with the upper surface of the solution while the jet nozzle is not operated, but is brought into contact with the upper surface of the solution while the upper surface of the solution is vibrated by the jet nozzle.

8. An apparatus according to claim 7, wherein said jet nozzle is provided in an upper portion of said washing vessel at a position higher than the upper surface of the solution filled in said washing vessel.

9. An apparatus according to claim 8, wherein said jet nozzle is covered by said cover when said cover is closed, and said cover has a portion that covers said jet nozzle at a position higher than the upper surface of the solution filled in said washing vessel.

10. An apparatus according to claim 9, wherein said washing vessel has a cover spray outlet configured to spray the same solution as the solution filled in said washing vessel onto the portion of said cover that covers said jet nozzle, said cover spray outlet being provided in the upper portion of said washing vessel at a position higher than the upper surface of the solution when the endoscope is immersed in the solution filled in said washing vessel.

11. An apparatus according to claim 10, wherein said cover spray outlet is formed on said jet nozzle.

12. An apparatus according to claim 7, wherein a height of an outer peripheral portion of said cover and a height of a supporting portion of said washing vessel that supports the outer peripheral portion of said cover are set to a level of the upper surface of the solution when said cover is closed and the endoscope is immersed in the solution filled in said washing vessel, and wherein a packing is provided between the outer peripheral portion of said cover and the supporting portion of said washing vessel.

13. An endoscope washing and disinfecting apparatus, comprising:

a washing vessel configured to contain an endoscope, and having a depth such that the endoscope is immersible in a predetermined solution filled in the washing vessel;

an openable and closable cover provided at an upper section of the washing vessel for covering an opening of the washing vessel; and an ultrasonic vibrator provided for the washing vessel for vibrating an upper surface of the solution when the cover is closed and the endoscope contained in the washing vessel is immersed in the solution filled therein, and while the endoscope is cleaned by a circulating effect of the solution;

wherein the cover has an inner surface set at a height such that when the cover is closed and the endoscope contained in the washing vessel is immersed in the solution filled therein, the inner surface of the cover is not brought into contact with the upper surface of the solution while the ultrasonic vibrator is not operated, but is brought into contact with the upper surface of the solution while the upper surface of the solution is vibrated by the ultrasonic vibrator.

\* \* \* \* \*